United States Patent [19]

Trono et al.

[11] Patent Number: 5,605,802
[45] Date of Patent: Feb. 25, 1997

[54] METHOD FOR IDENTIFYING AGENTS WHICH BLOCK INFECTION OF CELLS BY HIV

[75] Inventors: Didier P. Trono, Solana Beach; Christopher R. Aiken, Encinitas; Simon M. Swingler, San Diego; Philippe A. Gallay, Solana Beach, all of Calif.

[73] Assignee: The Salk Institute for Biological Studies, La Jolla, Calif.

[21] Appl. No.: 316,038

[22] Filed: Sep. 30, 1994

[51] Int. Cl.$^6$ .................................................. G01N 33/569
[52] U.S. Cl. .................. 435/7.4; 435/5; 435/7.2; 435/7.8; 435/7.92; 435/7.93; 435/7.94; 435/7.95; 435/15; 435/35; 435/974; 436/516
[58] Field of Search ................................ 435/5, 7.2, 7.4, 435/7.8, 7.92–7.95, 15, 35, 974; 436/516

[56] References Cited

PUBLICATIONS

Gallay et al. "HIV-1 Infection of Nondividing Cells: C-Terminal Tyrosine Phosphorlylation of the Viral Matrix Protein Is a Key Regulator" *Cell*, vol. 80, No. 3 (Feb. 10, 1995), pp. 379–388. QH573.
Burnette et al. "Phosphorylation of HIV-1 gag Proteins by Protein Kinase C" *The Journal of Biological Chemistry*, vol. 268, No. 12 (Apr. 25, 1993), pp. 8698–8703, QP501.J7.
Ruksen et al., "Nonradioactive Assays of Protein–Tyrosine Kinase Activity Using Anti–phosphotyrosine Antibodies" *Methods in Enzymology* 200:98–107 (1991).
Ferrari and Thomas, "Micro–and Macropurification Methods for Protein Kinases" *Methods in Enzymology* 200:159–169 (1991).
Schwedler et al., "The nuclear localization signal of the matrix protein of human immunodeficiency virus type 1 allows the establishment of infection in macrophages and quiescent T lymphocytes" *Proc. Natl. Acad. Sci.* 91:6992–6996 (1994).
Ronnstrand and Heldin, "Purification of Platelet–Derived Growth Factor β Receptor from Porcine Uterus" *Methods in Enzymology* 200:371–388 (1991).
Yu et al., "Vpx of simian immunodeficiency virus is localized primarily outside the virus core in mature virions" *Journal of Virology* 67:4386–4390 (1993).
Zack et al., "Incompletely reverse–transcribed human immunodeficiency virus type 1 genomes in quiescent cells can function as intermediates in the retroviral life cycles" *Journal of Virology* 66:1717–1725 (1992).
Zack et al., "HIV-1 entry quiesecnt primary lymphocytes: Molecular analysis reveals a labile, latent viral structure" *Cell* 61:213–222 (1990).
Zhou et al., "Identification of a membrane–binding domain within the amino–terminal region of human immunodeficiency virus type 1 Gag protein which interacts with acidic phospholids" *Journal of Virology* 68:2556–2569 (1994).
Trono, Didier, "Partial Reverse Transcripts in Virions from Human Immunodeficiency and Murine Leukemia Viruses" *Journal of Virology* 66:4893–4900 (1992).

Schwedler et al., "vif Is Crucial for Human Immunodeficiency Virus Type 1 Proviral DNA Synthesis in Infected Cells" *Journal of Virology* 67:4945–4955 (1993).
Sahal et al., "Solid–Phase Protein–Tyrosine Kinase Assay" *Methods in Enzymology* 200:90–97 (1991).
Stochaj and Silver, "A conserved phosphoprotein that specifically binds nuclear localization sequences is involved in nuclear import" *Journal of Cell Biology* 117:473–482 (1992).
Thelen et al., "Regulation by phosphorylation of reversible association of a myristoylated protein kinase C substrate with the plasma membrane" *Nature* 351:320–322 (1991).
Trono et al., "HIV–1 Gag mutants can dominantly interfere with the replication of the wild–type virus" *Cell* 59:113–120 (1989).
Varshavsky, A. "Naming a targeting signal" *Cell* 64:13–15 (1991).
Walker et al., "Translocation of pp60$^{c-src}$ from the plasma membrane to the cytosol after simulation by the platelet–derived growth factor" *The Journal of Biological Chemistry* 268:19552–19558 (1993).
Yu et al., "The matrix protein of human immunodeficiency virus type 1 is required for incorporation of viral envelope protein into mature virions" *Journal of Virology* 66:4966–4971 (1992).
Yu et al., "The C terminus of human immunodeficiency virus type 1 matrix protein is involved in early steps of the virus life cycle" *Journal of Virology* 66:5667–5670 (1992).
Yu et al., "Open Reading Frame vpr of Simian Immunodeficiency Virus Encodes a Virion–Associated Protein" *Journal of Virology* 64:5688–5693 (1990).
Yuan et al., "Mutations in the N–terminal region of human immunodeficiency virus type 1 matrix protein block intracellular transport of the Gag precursor" *Journal of Virology* 67:6387–6394 (1993).
Paxton et al., "Incorporation of Vpr into human immunodeficiency virus type 1 virions: requirement for the p6 region of gag and mutational analysis" *Journal of Virology* 67:7229–7237 (1993).
Richardson et al., "Nuclear location signals in polyoma virus large T" *Cell* 44:77–85 (1986).

(List continued on next page.)

*Primary Examiner*—Christine M. Nucker
*Assistant Examiner*—Jeffrey Stucker
*Attorney, Agent, or Firm*—Pretty, Schroeder, Brueggemann & Clark; Stephen E. Reiter; Robert T. Ramos

[57] ABSTRACT

In accordance with the present invention, there are provided novel assays which allow the identification of compounds which block the ability of lentiviruses to infect non-dividing cells. Compounds discovered employing the invention methods can be employed to block the ability of HIV to infect non-dividing cells. In accordance with another aspect of the present invention, novel antibodies have been developed which are specifically immunoreactive with the phosphorylated form of HIV-1 MA. In accordance with yet another aspect of the present invention, novel kinases which phosphorylate HIV-1 MA have been discovered.

12 Claims, No Drawings

OTHER PUBLICATIONS

Rihs and Peters., "Nuclear transport kinetics depend on phosphorylation-site-containing sequences flanking the karyophilic signal of the Simian virus 40 T-antigen" *EMBO* 7:1479–1484 (1989).

Roe et al., "Integration of murine leukemia virus DNA depends on mitosis" *EMBO Journal* 12:2099–2108 (1993).

Royer et al., "Functional domains of HIV-1 gag-polyprotein expressed in baculovirus-infected cells" *Virology* 184:417–422 (1991).

Schultz et al., "Fatty acylation of proteins" *Annual Review of Cell Biology* 4:611–647 (1988).

Schwedler et al., "vif is crucial for human immunodeficiency virus type 1 proviral DNA synthesis in infected cells" *Journal of Virology* 67:4945–4955 (1993).

Sharova and Bukrinskaya., "p17 and p17-containing gag precursors of input human immunodeficiency virus are transported into the nuclei of infected cells" *Aids Research and Human Retroviruses* 7:303–306 (1991).

Spina et al., "The importance of nef in the induction of human immunodeficiency virus type 1 replication from primary quiescent CD4 lymphocytes" *Journal of Experimental Medicine* 179:115–123 (1994).

Michaud and Goldfarb, "Most nuclear proteins are imported by a single pathway" *Experimental Cell Research* 208:128–136 (1993).

Miller et al., "The human immunodeficiency virus-1 nef gene product: A positive factor for viral ionfection and replication in primary lymphocytes and macrophages" *Journal of Experimental Medicine* 179:101–113 (1994).

Moll et al., "The role of phosphorylation and the CDC28 protein kinase in cell cycle-regulated nuclear import of the S. cerevisiae transcription factor SW15" *Cell* 66:743–758 (1991).

Morin et al., "Nuclear localization of the adenovirus DNA-binding protein: requirement for two signals and complementation during viral infection" *Mollecular and Cellular Biology* 9:4372–4380 (1989).

Ogawa et al., "Mutational analysis of the human immunodeficiency virus vpr open reading frame" *Journal of Virology* 63:4110–4114 (1989).

Okuno et al., "70–kDa heat–shock cognate protein colocalizes with karyophilic proteins into the nucleus during their transport in vitro". *Experimental Cell Research* 206:134–142 (1993).

Pandey and Parnaik, "Identification and characterization of nuclear location signal-binding protein in the nuclear envelopes" *Biochimica et Biophysica ACTA* 1063:81–89 (1991).

Lang., et al "Importance of vpr for infection of Rhesus monkeys with simian immunodeficiency virus" *Journal of Virology* 67:909–912 (1993).

Lavallee et al., "Requirement of the Pr55gag precursor for incorporation of the Vpr product into human immunodeficiency virus type 1 with viral particles" *Journal of Virology* 68:1926–1934 (1994).

Lavallee et al., "HIV-1 HxBc2 strain encodes a truncated vpr gene product of 78 amino acids" *Journal of Acquired Immune Deficiency Syndromes* 6:529–530 (1993).

Levy et al., "Induction of cell differentiation by human immunodeficiency virus 1 vpr" *Cell* 72:541–550 (1993).

Lewis and Emerman, "Passage through mitosis is required for oncoretroviruses but not for the human immunodeficiency virus" *Journal of Virology* 68:510–516 (1994).

Lewis et al., "Human immunodeficiency virus infection of cells arrested in the cell cycle" *EMBO Journal* 11:3053–3058 (1992).

Li et al., "Intracellular distribution of a nuclear localization signal binding protein" *Experimental Cell Research* 202:355–365 (1992).

Lu et al., "Human immunodeficiency virus type 1 viral protein R localization in infected cells and virions" *Journal of Virology* 67:6542–6550 (1993).

Meltzer et al., "Role of mononuclear phagocytes in the pathogenesis of human immunodeficiency virus infection" *Annual Review of Immunology* 8:169–194 (1990).

Michaud and Goldfarb, "Microinjected U snRNAs are imported to oocyte nuclei via the nuclear pore complex by three distinguishable targeting pathways" *The Journal of Cell Biology* 116:851–861 (1992).

Gao et al., "Low levels of deoxynucletides in peripheral blood lyumphocytes: A strategy to inhibit human immunodeficiency virus type 1 replication" *Proc. Natl. Acad. Sci. USA* 90:8925–8928 (1993).

Garcia-Bustos et al., "Nuclear protein localization" *Biochimica et Biophysica ACTA* 1071:83–101 (1991).

Gelderblom, H. R. "Assembly and morphology of HIV: Potential effect of structure on viral function" AIDS 5:617–638 (1991); and Arnold and Arnold, *Advances in Virus Research* 39:1–87 (1991).

Graziadei et al., "Introduction of unlabled proteins into living cells by electroporation and isolation of viable protein-loaded cells using dextran-fluorescein isothiocynate as a marker for protein uptake" *Analytical Biochemistry* 194:198–203 (1991).

Gulizia et al., "Reduced nuclear import of human immunodeficiency virus type 1 preintegration complexes in the presence of a prototypic nuclear targeting signal" *Journal of Virology* 68:2021–2025 (1994).

Hagiwara et al., "Transcriptional attenuation following cAMP induction requires PP-1 mediated dephosphorylation of CREB" *Cell* 70:105–113 (1992).

Hattori et al., "The human immunodeficiency virus type 2 vpr gene is essential for productive infection of human macrophages" *Proc. Natl. Acad. Sci. USA* 87:8080–8084 (1990).

Heinzinger et al., "The Vpr protein of human immunodeficiency virus type 1 influence nuclear localization of viral nucleic acids in nondividing host cells" *Proc. Natl. Acad. Sci. USA* 91:7311–7315 (1994).

Kalderon et al., "A short amino acid sequence able to specify nuclear location" *Cell* 39:499–509 (1984).

Cohen et al., "Human immunodeficiency virus vpr product is a virion-associated regulatory protein" *Journal of Virology* 64:3097–3099 (1990).

Dang and Lee, "Identification of the human c–myc protein nuclear translocation signal" *Molecular and Cellular Biology* 8:4048–4054 (1988).

Dedera et al., "Viral protein R of human immunodeficiency virus types 1 and 2 is dispensable for replication and cytopathgenicity in lymphoid cells" *Journal of Virology* 63:3205–3208 (1989).

Dingwall and Laskey, "Nuclear targeting sequence—a consensus?" *The Journal of Cell Biology* 116:851861 (1992).

Dorfman et al., "Role of the matrix protein in the virion association of the human immunodeficiency virus type 1 envelope glycoprotein" *Journal of Virology* 68:1689–1696 (1993).

Duronio et al., "Reconstitution of protein N–myristoylation in *Escherichia coli*" *Methods: A Companion to Methods in Enzymology* 1:253–263 (1990).

Facke et al., "A large deletion in the matrix domain of the human immunodeficiency virus gag gene redirects virus particle assembly from the plasma membrane to the endoplasmic reticulum" *Journal of Virology* 67:4972–4980 (1993).

Forbes, D. J., "Structure and function of the nuclear pore complex" *Annual Review of Cell Biology* 8:495–527 (1992).

Adam and Gerace, "Cytosolic proteins that specifically bind nuclear location signals are receptors for nuclear import" *Cell* 66:837–847 (1991).

Arnold and Arnold, "Human immunodeficiency virus structure: implications for antiviral design" *Advances in Virus Research* 39:1–87 (1991).

Bray et al., "A small element from the Mason–Pfizer monkey virus genome makes human immunodeficiency virus type 1 expression and replication Rev–independent" *Proc. Natl. Acad. Sci. USA* 91:1256–1260 (1994).

Bukrinsky et al., "Association of integrase, matrix, and reverse transcriptase antigens of human immunodeficiency virus type 1 with viral nucleic acids following acute infection" *Proc. Natl. Acad. Sci. USA* 90:6125–6129 (1993).

Bukrinsky et al., "Active nuclear import of human immunodeficiency virus type 1 preintegration complexes" *Proc. Natl. Acad. Sci. USA* 89:6580–6584 (1992).

Bukrinsky et al., "Quiescent T lymphocytes as an inducible virus reservoir in HIV–1 infection" *Science* 254:423–427 (1991).

Bukrinsky et al., "A nuclear localization signal within HIV–1 matrix protein that governs infection of non–dividing cells" *Nature* 365:666–669 (1993).

Burnette et al., "Phosphorylation of HIV–1 gag proteins by protein kinase C." *Journal of Biological Chemistry* 268:8698–8703 (1993).

Charneau et al., "A second origin of DNA plus–strand synthesis is required for optimal human immunodeficiency virus replication" *Journal of Virology* 66:2814–2820 (1992).

METHOD FOR IDENTIFYING AGENTS WHICH BLOCK INFECTION OF CELLS BY HIV

FIELD OF THE INVENTION

The present invention relates to methods for the identification of compounds which block infection of non-dividing cells by lentiviruses such as human immunodeficiency virus (HIV). In another aspect, the present invention relates to antibodies useful in such methods. In yet another aspect, the present invention relates to novel kinases which selectively phosphorylate specific residues of the HIV-1 matrix protein.

BACKGROUND OF THE INVENTION

Retroviruses are enveloped, single-stranded RNA viruses whose replication depends on the integration of a double-stranded DNA intermediate, termed the provirus, into the host cell genome. Onco-retroviruses, such as the murine leukemia virus (MuLV), depend on cell proliferation for completion of their life cycle (Humphries and Temin, *Journal of Virology* 10:82–87 (1972); and Humphries and Temin, *Journal of Virology* 14:531–546 (1974)). The breakdown of the nuclear envelope that accompanies mitosis is essential to bring the MuLV preintegration complex into the vicinity of the host cell chromosome, allowing integration of the viral genome into the host cell chromosome (Lewis and Emerman, *Journal of Virology* 68:510–516 (1994); and Roe et al., *EMBO Journal* 12:2099–2108 (1993)).

In sharp contrast, lentiviruses (including HIV) are distinguished by their ability to infect non-dividing cells. For instance, HIV-1 replicates in terminally differentiated tissue macrophages (Meltzer et al., *Annual Review of Immunology* 8:169–194 (1990)), as well as in cells that are artificially arrested in the G1/S or G2 phases of the cell cycle (Lewis and Emerman supra; and Lewis et al., *EMBO Journal* 11:3053–3058 (1992)). A critical determinant of this property has been mapped to the HIV-1 matrix (MA) protein, one of the virus structural components encoded by the gag gene (Bukrinsky et al., *Nature* 365:666–669 (1993)).

MA is the N-myristoylated cleavage product of the HIV-1 p55 Gag precursor by the virally-encoded protease. MA plays a key role in retroviral assembly, by directing the intracellular transport and membrane association of the Gag polyprotein (Varmus and Swanstrom, *In: RNA Tumor Viruses*, Weiss, et al., eds (Cold Spring Harbor Laboratory, Cold Spring Harbor, N.Y.) 369–512 (1982); Yuan et al., *Journal of Virology* 67:6387–6394 (1993); Zhou et al., *Journal of Virology* 68:2556–2569 (1994); and Facke et al., *Journal of Virology* 67:4972–4980 (1993)), and by facilitating the recruitment of the viral envelope into viral particles (Yu et al., *Journal of Virology* 66:5966–5971 (1992); and Dorfman et al., *Journal of Virology* 68:1689–1696 (1994)). MA also appears to participate in the early steps of the viral life cycle (Yu et al., *Journal of Virology* 66:5667–5670 (1992)).

In lentiviruses, MA contains a stretch of highly conserved amino acids, for example, Gly-Lys-Lys-Lys-Tyr-Lys (SEQ ID NO:1) in HIV-1 (Myers et al. eds. *Human Retroviruses and AIDS 1992: A Compilation and Analysis of Nucleic Acid and Amino Acid Sequences* (Los Alamos National Laboratory, Los Alamos, N.M.) (1992)). This conserved sequence closely resembles the SV40 large T antigen nuclear localization signal (NLS) (Kalderon et al., *Cell* 39:499–509 (1984)). Indeed, the HIV-1 MA NLS peptide has been shown to act as a nuclear import signal when coupled to a heterologous protein in vitro (Bukrinsky supra). In addition, an HIV-1 strain mutated in the MA-NLS-coding sequence could not infect cells arrested in the cell cycle, thus displaying a phenotype more characteristic of an onco-retrovirus (Bukrinsky supra). The defect was associated with a failure to induce viral two-LTR circular DNA in growth-arrested cells. Because this form of DNA is generated only after the viral preintegration complex migrates to the nucleus, this result indicated further that the MA NLS plays a role in the infection process. These findings corroborated the earlier detection of MA in purified HIV-1 preintegration complexes (Bukrinsky et al., *Proc. Natl. Acad. Sci. U.S.A.* 90:6125–6129 (1993)) as well as in the nucleus of newly infected cells (Sharova and Bukrinskaya., *AIDS Research and Human Retroviruses* 7:303–306 (1991)), and led to the postulate that the HIV-1 MA NLS might be critical for infection of macrophages. Indeed, this has recently been demonstrated by the showing that HIV-1 MA NLS mutants replicate with normal kinetics in dividing cells, including activated peripheral blood lymphocytes (PBL), but do not grow efficiently in terminally differentiated primary macrophages. Furthermore, it has recently been discovered that MA NLS mutants cannot establish a stable and inducible infection intermediate in unstimulated PBL (von Schwedler et al., *Proc. Natl. Acad. Sci. U.S.A.* 91:6992–6996 (1994)).

For infection of non-dividing cells, the HIV-1 preintegration complex must cross the nuclear envelope. Most but not all proteins migrating to the nucleus contain amino acid sequences at least vaguely related to the archetypal nuclear localization signal (NLS) of SV40 large T antigen NLS (i.e., PKKKRKV; SEQ ID NO:2; see Dingwall and Laskey, *TIPS* 16:478–481 (1991)). Transport of macromolecules across nuclear envelope can be divided into two distinct steps (reviewed in Forbes, D. J., *Annual Review of Cell Biology* 8:495–527 (1992)). The initial reaction includes the formation of a complex between the karyophile and a cytoplasmic NLS receptor, or Nu-transferon (Varshavsky, A., *Cell* 64:13–15 (1991)). Putative NLS receptors have been identified by NLS ligand binding and crosslinking studies, as well as through the functional reconstitution of import NLS-containing karyophiles in permeabilized cell assays (Adam and Gerace, *Cell* 66:837–847 (1991); Liet al., *Experimental Cell Research* 202:355–365 (1992); Okuno et al., *Experimental Cell Research* 206:134–142 (1993); Pandey and Parnaik, *Biochimica et Biophysica ACTA* 1063:81–89 (1991); and Stochaj and Silver, *Journal of Cell Biology* 117:473–482 (1992)). None of these receptors, however, has been cloned.

NLS-mediated nuclear import can be kinetically saturated by microinjecting high concentrations of synthetic T-antigen NLS peptide. NLS peptide competes the nuclear migration of a large number of cellular karyophiles, indicating that most of these are imported by a single pathway (Michaud and Goldfarb, *Experimental Cell Research* 208:128–136 (1993)). Nuclear migration of the HIV-1 preintegration complex obeys the same rules, in being an energy dependent process which can be competed with NLS peptide (Bukrinsky et al., *Proc. Natl. Acad. Sci. U.S.A.* 89:6580–6584 (1992); and Gulizia et al., *Journal of Virology* 68:2021–2025 (1994)); this corroborates the demonstrated role of the MAN LS in this process.

The mechanisms developed by HIV-1 to infect non-dividing cells are most likely essential for the spread of this virus in infected individuals, and for AIDS pathogenesis. As such, the various steps involved in the completion of this process represent highly suitable targets for the development of novel antiviral therapies. In addition, the resulting knowledge might have broader implications, in the field of gene therapy. Indeed, the stable expression of foreign genes is often desirable in cells which enter mitosis at a low frequency (such as myocytes or even hepatocytes), or do not divide at all (such as macrophages and neurons).

Because conventional retroviral vectors cannot efficiently infect such targets, alternatives are being sought. Non-retroviral vectors are one option. Adenovirus-based vectors are promising, but their failure to stably integrate into the genome of target cells limits their use, because transgenes are only transiently expressed. In contrast, vectors derived from adeno-associated virus do integrate; however, it has so far been extremely difficult to generate high titer stocks of these vectors, whereas this is a prerequisite for efficient gene transfer. Alternative strategies have therefore been developed to allow the use of simple retroviral vectors in cells which rarely divide.

For instance, partial hepatectomies are performed to enhance the uptake of MuLV-based vectors by regenerating hepatocytes. Also, cells such as myocytes are induced to proliferate ex vivo, infected with retroviral vectors while dividing, and then re-implanted. However, such techniques cannot be applied in a number of cell types, such as neurons. Furthermore, even when genes are efficiently transferred, a major problem remains that most often their expression is only transient. Although the mechanism of this silencing is yet unclear, one can speculate that the reorganization of the chromatin, which takes place when a cell passes from a dividing to a resting state, plays a critical role in this process. Indeed, it could be that regions of the genome in which retroviruses preferentially integrate, when cells are dividing, subsequently become transcriptional "cold-spots" when they stop proliferating.

Accordingly, it might be preferable to transfer genes in a context reproducing the in vivo state of the cell. This could be done if retroviral vectors with the properties of lentiviruses were available. In view of these considerations, the lessons learned from studying HIV-1 infection of non-dividing targets are expected to one day help make very significant progress in the field of gene therapy. Ironically, one area which might directly benefit from this progress is that of approaches based on anti-HIV intracellular immunization, where one requirement is to reach the same non-dividing cells which can be infected by the virus itself.

BRIEF DESCRIPTION OF THE INVENTION

In accordance with the present invention, we have developed novel assays which allow the identification of compounds which block the ability of lentiviruses to infect non-dividing cells. Compounds discovered employing the invention methods can be employed to block the ability of HIV to infect non-dividing cells. Thus, infected individuals could be treated with compound identified by the invention method in an amount effective to prevent phosphorylation of human immunodeficiency virus type 1 Matrix protein (MA), thereby preventing further proliferation of the virus.

In accordance with another aspect of the present invention, we have developed novel antibodies which are specifically immunoreactive with the phosphorylated form of HIV-1 MA.

In accordance with yet another aspect of the present invention, we have discovered novel kinases which phosphorylate HIV-1 MA.

DETAILED DESCRIPTION OF THE INVENTION

In accordance with the present invention, there are provided methods for identifying compounds that inhibit phosphorylation of human immunodeficiency virus type 1 Matrix protein (MA). By inhibiting the phosphorylation of MA, infection of non-dividing cells by HIV is prevented. Invention method comprises:

exposing MA to phosphorylation conditions independently in the presence, and in the absence, of test compound, and identifying those test compounds which inhibit phosphorylation of MA upon exposure thereto.

Alternatively, invention method can be carried out as a competitive assay, wherein MA is exposed to phosphorylation conditions in the presence of varying amounts of test compound, and changes in the level of phosphorylation of MA as a result of exposure of MA to varying amounts of test compound are detected.

MA contemplated for use in the practice of the present invention can be obtained from a variety of sources, such as, for example, from HIV-infected cells, from HIV particles, from mammalian cells infected with an MA-expression vector, by recombinant production (for example, in *E. coli*, baculovirus, and the like), as well as peptide fragments thereof. Peptide fragments contemplated for use herein contain the tyrosine and/or serine residues identified herein as being phosphorylated by HIV. Thus, for example, myristoylated recombinant MA can be generated by *E. coli*, or by co-expression of *Saccharomyces cerevisiae* myristoyl-CoA:protein N-myristoyl-transferase, as described by Duronio et al., *In: METHODS: A Companion to Methods in Enzymology* 1:253–263 (1990)). This protein, as well as unmodified recombinant MA, can then be kinased in vitro. Presently preferred MA employed in the invention screening method is recombinantly produced.

As employed herein, the phrase "phosphorylation conditions" refers to conditions of time, temperature, media, and the like, which facilitate phosphorylation of tyrosine and/or serine residues of HIV-1 MA. Such conditions can be provided in a variety of ways, such as, for example, by contacting MA with a suitable cell extract, e.g., cell extract derived from human T cell lines, fibroblasts, epithelial cells, serum, and the like.

Test compounds suitable for use in the invention screening method can be readily identified by those of skill in the art. For example, test compounds can be selected from known classes of pharmacologically active agents, such as antibiotics, anti-fungal agents, anti-neoplastic agents, enzymatically active agents, immunostimulating agents, immunosuppressive agents, and the like. Those of skill in the art can readily identify additional categories of compounds suitable for use in the practice of the present invention. For example, test compounds contemplated for use in the practice of the present invention include proteoglycans (e.g., heparin), ribosides (e.g., benzimidazole riboside, 5,6-dichlorobenzimidazole riboside), Sarc inhibitors (e.g., herbimycin), and the like.

Suitable concentrations of test compound for use in the invention screening method can be readily determined by those of skill in the art. Typically, MA is contacted with test compound at a concentration in the range of about 0.01 nM up to 10 μM.

As can be readily determined by those of skill in the art, phosphorylation of MA can be detected in a variety of ways. Thus, for example, techniques such as ELISA, Western blot, uptake of labelled phosphate, and the like can be employed.

Compounds identified employing invention assay methods can be applied in a variety of ways. For example, such a compound can be employed to block the ability of HIV to infect a cell. This could be accomplished by treating said cell with compound identified by the invention method in an amount effective to prevent phosphorylation of human immunodeficiency virus type 1 Matrix protein (MA).

In accordance with another embodiment of the present invention, there are provided antibodies which are specifically immunoreactive with $Y_{132}$ phosphorylated human immunodeficiency virus type 1 Matrix protein (i.e., wherein the tyrosine residue at position 132 of MA is phosphorylated). Invention antibodies are substantially non-reactive with HIV-1 MA wherein the tyrosine residue at position 132 thereof has not been phosphorylated. Indeed, reference to invention antibodies as specifically immunoreactive with $Y_{132}$ phosphorylated HIV-1 MA further reflects the fact that such antibodies do not immunoreact with any other proteins containing phosphorylated tyrosine residues.

Antibodies of the invention can be either polyclonal or monoclonal. Those of skill in the art are well aware of suitable techniques for the preparation of such antibodies. Thus, for example, the above-described antibodies can be prepared employing standard techniques, as are well known to those of skill in the art, using the phosphorylated form of HIV-1 MA, or phosphorylated peptide fragments thereof (so long as said peptide fragments contain the tyrosine and/or serine residues identified herein as being phosphorylated by HIV), as antigen for antibody production. Antibodies of the present invention are typically produced by immunizing a mammal with an inoculum containing the phosphorylated form of HIV-1MA, or suitable phosphorylated fragment thereof, thereby inducing the production of antibody molecules having immunospecificity therefor.

As a specific example, antibodies to a particular phosphorylated form of HIV-1 MA, or to a particular phosphorylated fragment thereof, may be obtained by immunizing three month old male and female white New Zealand rabbits with a synthetic peptide antigen whose C-terminal tyrosine residue is phosphorylated. The reaction mixture is dialyzed to remove low molecular weight material, and the retentate is frozen in liquid nitrogen and stored at −20° C. Animals are immunized with the equivalent of 1 mg of the antigen according to the procedure of Benoit et al. *P.N.A.S. U.S.A.* 79:917–921 (1982). At four week intervals, the animals are boosted by injections of 200 μg of the antigen and bled ten to fourteen days later. After the third boost, antiserum is examined for its capacity to bind radioiodinated antigen and then purified by CMC-ion exchange column chromatography. Antibody is then collected from the immunized mammal and isolated to the extent desired by well known techniques such as, for example, by using DEAE Sephadex to obtain the IgG fraction.

To enhance specificity, the antibody may be purified by immunoaffinity chromatography using solid-phase immunizing polypeptide. The antibody is contacted with the solid-phase immunizing polypeptide for a period of time sufficient for the polypeptide to immunoreact with the antibody molecules to form a solid-phase immunocomplex. The bound antibodies are then separated from the complex by standard techniques.

Antibody so produced can be used, inter alia, in diagnostic methods and systems to detect the level of phosphorylated HIV-1 MA present in a mammalian, preferably human, body sample, such as tissue or vascular fluid. The anti-phosphorylated HIV-1 MA antibodies can also be used for immunoaffinity or affinity chromatography purification of the phosphorylated form of HIV-1 MA from biological materials. In addition, anti-phosphorylated HIV-1 MA antibodies according to the present invention can be used in mammalian therapeutic methods, preferably human, as an agonist or antagonist, to neutralize or modulate the ability of phosphorylated HIV-1 MA to induce infection of quiescent cells.

In accordance with yet another embodiment of the present invention, there are provided substantially pure kinases which selectively phosphorylate the tyrosine residue at position 132 of human immunodeficiency virus type 1 Matrix protein (MA), wherein said kinase is a membrane-associated, cytoplasmic protein.

Use of the phrase "substantially pure", "isolated" or "recombinantly produced" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways that the DNAs, RNAs, polypeptides or proteins as they naturally occur are not, such as identification of selective drugs or compounds.

In order for infection of non-dividing cells to occur, the HIV-1 preintegration complex must enter the cell nucleus. The HIV-1 preintegration complex is composed of a number of components, including HIV-1 matrix protein (MA). MA, a cleavage product of the HIV-1 p55 Gag precursor, undergoes post-translational myristoylation. Although HIV-1 MA contains a nuclear localization signal (NLS), it does not localize to the nucleus of cells in which it is expressed, but is instead directed to the plasma membrane by N-terminal myristoylation. Indeed, previous analyses have shown that MA in virions is predominantly located under the lipid bilayer, in association with the viral envelope (Gelderblom, H. R., *AIDS* 5:617–638 (1991); and Arnold and Arnold, *Advances in Virus Research* 39:1–87 (1991)).

In accordance with the present invention, it has been discovered that MA undergoes, at the time of viral assembly, a modification which overrides the dominant effect of myristoylation, thereby revealing the nuceleophilic function of the protein. Indeed, in accordance with the present invention, it has been discovered that phosphorylation of MA at a single tyrosine residue and optionally at one major serine residue (at residue 67, 72 or 77)), which occurs late during viral assembly, releases the phosphorlyated protein into the cytosol. Once released from the cell membrane by phosphorylation, the MA NLS becomes functional nto direct preintegration complex into the nucleus of the target cell. Thus, in accordance with the present invention, it has been found that mutant virus in which the critical tyrosine residue is replaced by a phenylalanine residue is defective for growth in macrophages, due to a block in nuclear import. This observation confirms that MA tyrosine-phosphorylation is important for HIV-1 infection of non-dividing cells.

Thus, in the course of research related to the present invention, it has been discovered that phosphorylation of MA specifically at tyrosine residue 132 facilitates transport of the HIV-1 pre-integration complex into the nucleus of macrophages. This modification is also believed to be important for the establishment of infection in quiescent T lymphocytes, and for infection of growth-arrested cells. Infection of quiescent T cells can be performed, for example, as described by Zack et al., in *Cell* 61:213–222 (1990), and Gao et al., *in Proc. Natl. Acad. Sci. U.S.A.* 90:8925–8928 (1993). Infection of growth-arrested $CD4^+$ MT4 cells can be done essentially as described by Heinzinger et al., supra. In brief, cells can be synchronized by isoleucine deprivation for 48 hours and then released into complete medium or in medium containing mimosine (400 μM), a plant amino acid that arrests the cell cycle at the $G_1/S$ boundary. Cells are then infected 42 hours after release from isoleucine deprivation. Viral DNA synthesis and nuclear import is monitored by PCR, with primers specific for the various intermediates and products of reverse transcription (see Trono in *J. Virology* 66:4893–4900 (1992) and von Schwedler et al., in *J. Virology* 67:4945–4955 (1993) for information regarding PCR primers useful for this purpose).

In the course of research related to the present invention, it has been demonstrated that a mutant HIV-1 strain defective in MA tyrosine phosphorylation is incompetent for growth in terminally differentiated macrophages. In the course of research related to the present invention, it has also been discovered that MA undergoes tyrosine phosphorylation at the time of viral assembly and that this modification positively regulates the karyophilic properties of MA. This was confirmed by showing that $Y_{132}$ phosphorylated HIV-1 MA molecules, which represent only about 1% of all MA molecules present in virions, are selectively imported into the nucleus of cells newly infected with HIV.

Thus, virion-associated MA can be immunoprecipitated with anti-phosphotyrosine antibodies; the pellet and the supernatant can then be analyzed by Western blot using a parallel i) anti-p17 antibody, to calculate the percentage of MA molecules containing phosphotyrosine, and ii) anti-phosphotyrosine antibody, to verify the efficiency of immunodepletion, and indicate whether repeated rounds of immunoprecipitation are necessary. Antibodies reacting specifically with serine-phosphorylated MA can readily be generated through the use of phosphorylated peptides, as recently done for the CREB transcription factor (see Hagiwara et al., *Cell* 70:105–113 (1992)). It is of note that MA is the only phosphotyrosine-containing protein that has been detected in virions.

Native and phosphorylated polypeptides can then be injected in the cytoplasm of 293 cells or of Xenopus oocytes. Injected cells can be analyzed by immunofluorescence staining and confocal microscopy (for 293 cells), or by immunoblot analysis of nuclear and cytoplasmic fractions (for Xenopus oocytes). NLS and phosphorylation mutants of MA, as well as cells injected in the presence of NLS peptide or WGA, can serve as controls. Such experiments indicate that phosphorylation of MA regulates the karyophilic properties of MA by triggering its release from cell membranes.

It has been established that HIV-1 MA is phosphorylated on serine and tyrosine residues, independently from the expression of the viral RT, IN, vif, vpr, vpu, env and nef genes. Furthermore, it has been shown that i) MA tyrosine phosphorylation requires membrane association and cleavage of the protein, ii) MA-specific serine and tyrosine kinase activities are associated with HIV-1 particles, iii) MA can be phosphorylated in vitro by incubation with membrane-enriched cellular extracts or conditioned medium, and iv) MA does not auto-phosphorylate.

This evidence indicates that a cellular kinase is responsible for MA phosphorylation.

Purified preparations of various kinases can be readily prepared using methods well known in the art (see, for example, Ferrari and Thomas *In: METHODS IN ENZYMOLOGY*, vol. 200, pp. 159–169, Hunter & Sefton, eds., Academic Press, 1991).

A recent report, based on the study of cells infected by Gag-expressing vaccinia vectors, indicated that MA might be phosphorylated by PKC (Burnette et al., *Journal of Biological Chemistry* 268:8698–8703 (1993)). However, several important differences can be noted between the published work and the analyses described herein, done in the more natural context of HIV-1 infected cells. For instance, the published study did not detect tyrosine phosphorylation of MA. In addition, the phosphopeptide mapping analyses described herein indicate that serine 110, the target of PKC according to the published report, is clearly not the residue which is phosphorylated in vivo.

As readily recognized by those of skill in the art, a wide variety of inhibitors (including commercially available inhibitors) of serine/tyrosine kinases can be evaluated in the MA in vitro kinase assays described herein, using conditioned medium as source of the kinase. The finding that a given inhibitor blocks MA phosphorylation would suggest that the MA-specific kinase of the invention is related to other kinases that are also inhibited by this particular agent.

Recombinant His-tagged MA, bound to a nickel column, can be used for affinity purification of the kinase. Thus, conditioned medium (rich in kinase activity) can be passed onto the column, and the washes and eluate tested for their respective content in MA-specific kinase.

MA-specific kinase activity can be isolated and/or purified from membrane-enriched cell extracts or from conditioned medium, using conventional techniques (fractionation on various columns, HPLC, etc). Virions can also be considered as a possible source of MA-specific kinase activity, since they are enriched in kinase activity. Eluate from the various columns or fractions can then be assayed for their ability to phosphorylate recombinant MA. Ultimately, the kinase can be purified to a point allowing micropeptide sequencing employing standard techniques therefor.

The invention will now be described in greater detail by reference to the following non-limiting examples.

EXAMPLE 1

Non-myristoylated MA, but not wild-type MA, is found in the nuclear fraction of cells transfected with HIV-1 proviral constructs Two forms of non-myristoylated MA were generated in the context of a full-length provirus. In one construct, the first glycine in MA was replaced by an alanine. In the second construct, a histidine hexamer was introduced at the N-terminal end of GAG; in addition to preventing myristoylation, the latter modification allows the easy recovery of MA by affinity purification on nickel columns. Human fibroblastic 293 cells were transfected with the various constructs. Cellular extracts of the transfected cells were prepared and subsequently separated into nuclear and cytoplasmic fractions. The resulting fractions were analyzed by Western blot with MA-specific antibody. Wild-type MA has an apparent MW of 17kDa; non-myristoylated MA, due to the presence of an N-terminal histidine tag, migrates as an 18kDa protein. Probing with a tubulin-specific antibody allowed verification of fractionation efficiency. Replacement of the N-terminal glycine by alanine gave a result identical to that obtained with the His-tagged protein.

These results reveal that myristoylated MA is found exclusively in the cytoplasmic compartment of transfected cells, whereas large amounts of non-myristoylated MA are associated with the nuclear fraction.

Even though HIV-1 MA contains a nuclear localization signal (NLS) sequence, which is capable of acting as a nuclear import signal, migration of the viral pre-integration complex to the nucleus of non-dividing cells is not observed when MA is myristoylated. It is only in the absence of myristoylation that migration into the cell nucleus, facilitated by the presence of the MA NLS as part of the pre-integration complex, is observed. Indeed, MA has not been reported to localize to the nucleus of HIV-infected cells, but instead to associate with the plasma membrane through a myristate residue bound to its N-terminal glycine. This suggests that the myristoylated sequence acts as a dominant targeting signal, which overcomes the potential for nuclear migration conferred by the NLS. Consistent therewith, studies in baculovirus have shown that unmyristoylated forms of the HIV-1 Gag precursor are directed to the cell nucleus, whereas normally myristoylated forms are found only in the cytoplasm and at the cell membrane (Royer et al., *Virology* 184:417–422 (1991)).

EXAMPLE 2

HIV-1 MA undergoes tyrosine phosphorylation at the time of viral assembly

The results presented in the previous Example indicate that MA has intrinsic nucleophilic properties, but that these intrinsic properties are masked by myristoylation of the protein. Yet, when HIV-1 enters target cells, the MA NLS is functional, playing a major role in allowing nuclear import of the viral preintegration complex. This suggests that changes occur between particle formation and virus entry, revealing the karyophilic potential of MA. N-myristoylation is a "permanent" modification; the half-life of the acyl chain moiety is equivalent to that of the polypeptide backbone (Schultz et al., *Annual Review of Cell Biology* 4:611–647 (1988)). However, the association of myristoylated MA with membranes appears to depend not only on myristate, but also on electrostatic forces contributed by nearby positively charged residues (Kalderon et al., supra). Use of an electrostatic mechanism implies that reversible membrane binding could be achieved by introduction of appropriately placed negative charges into the protein.

Thus, the phosphorylation status of HIV-1 MA was examined. Viral proteins from cytoplasmic extracts of transfected cells or purified virions were tested by Western blot, with MA- or phosphotyrosine-specific antibodies. The proviral constructs used include: R7 (wild type), $MA_{G2A}$.R7 (which produces non-myristoylated Gag), $MA_{Y29F}$.R7 (wherein a phenylalanine (F) is substituted for tyrosine (Y) at residue 29), $MA_{Y86F}$.R7 (wherein F is substituted Y at residue 86), and $MA_{Y132F}$.R7 (wherein F is substituted Y at residue 132). p55 Gag precursor was not found to react with anti-phosphoryrosine antibody. Accordingly, no phosphotyrosine-containing Gag was observed after transfection with a protease-defective provirus.

In HIV-1 virions purified from acutely or chronically infected T cell lines, MA was observed to react with anti-phosphotyrosine antiserum in Western blots. MA has four tyrosine residues, at positions 29, 79, 86 and 132, all of which are potential targets for phosphorylation. Each of these tyrosines was subjected to site-directed mutagenesis and changed to phenylalanine, in the context of a proviral construct. The resulting virions were then analyzed by anti-phosphotyrosine Western blotting. This identified the C-terminal tyrosine residue (i.e., $Y_{132}$) as the only phosphorylated tyrosine in MA. The timing of this post-translational modification was then analyzed. Eliminating either myristoylation or processing of Gag by site-directed mutagenesis of the MA or protease genes, respectively, totally prevented the tyrosine phosphorylation of MA. These results thus indicate that MA tyrosine phosphorylation is a late maturation event, since it requires both membrane association and proteolytic cleavage of Gag.

EXAMPLE 3

Tyrosine-phosphorylated MA is rapidly imported to the nucleus of cells acutely infected with HIV-1

Tyrosine-phosphorylated MA is detected in virions, yet it appears to constitute only a small fraction of all MA molecules contained in the particle. Based on the suspicion that this enzymatic modification is responsible for the karyophilic properties of MA, cells acutely infected with HIV-1 were fractionated into cytoplasmic and nuclear fractions, at various times after infection (i.e., at 0, 1, 2, 3 and 6 hours). These fractions were then analyzed by Western blot, with MA- and phosphotyrosine-specific antibodies. Whereas the bulk of MA stays in the cytoplasm, all tyrosine-phosphorylated MA molecules are rapidly imported to the nucleus.

These results reveal that, within three hours of infection, all tyrosine-phosphorylated MA molecules are transported to the nucleus, whereas the bulk of unphosphorylated MA (i.e., not phosphorylated on tyrosine), remains associated with the cytoplasm. These data therefore confirm the existence of a crucial link between MA tyrosine phosphorylation and HIV-1 nuclear import.

EXAMPLE 4

An HIV-1 strain defective for MA tyrosine phosphorylation is blocked for growth in terminally differentiated macrophages, due to a defect in nuclear import Based on the results obtained in Example 3, additional experiments were conducted to determine whether MA tyrosine phosphorylation is important for HIV-1 infection of non-dividing cells. Thus, growth of ΔNLS mutant viruses ($MA_{KK277TT}$.R7-BaL; $MA_{K30A}$.R7.BaL) and phosphotyrosine-defective virus ($MA_{Y132F}$.R7-BaL) are compared with the wild-type MA parental strain, in terminally differentiated macrophages. Additional controls were provided by infecting cells with the wild-type-MA (R7-BaL) virus, in the presence of NLS or reverse peptide.

Substituting phenylalanine for the carboxy-terminal tyrosine of MA in a viral mutant designated $MA_{Y132F}$R7 (which also encodes a 78-amino-acid-long Vpr protein) did not alter growth of the resulting HIV-1 mutant in dividing cells. However, this variant is unable to replicate in terminally differentiated macrophages. MA-phosphotyrosine-mutant HIV-1 is also unable to replicate in macrophages.

Moreover, PCR analysis of freshly infected macrophages (i.e., infected with wild-type-MA (R7.BaL), phosphotyrosine-defective ($MA_{Y132F}$.R7.BaL) or ΔNLS ($MA_{KK277TT}$.R7BaL) viruses) at 3, 8, 24, 32 and 48 hours post-infection revealed that the defect in the ability to phosphorylate is due to a block in nuclear import, as $MA_{Y132F}$R7 presents the same phenotype as an MA NLS mutant, inducing normal amounts of full-length viral linear DNA, yet strikingly decreased levels of viral DNA circles, compared to wild-type.

PCR analysis was carried out employing the following primer pairs—Vif6/Vif7 and LTR5/5NC2 (see Trono supra and von Schwedler et al. supra for details on these primer pairs). Primer pair Vif6/Vif7 amplifies elongated minusstrand DNA, primer pair LTR5/5NC2 detects DNA molecules synthesized after the second template switch, and primer pair LTR8/LTR9 is specific for two-LTR circles.

Phosphotyrosine-defective and ΔNLS mutant viruses induce wild-type levels of linear DNA, but dramatically reduced amounts of circles. Taken together, these data allow one to conclude that tyrosine phosphorylation at the time of assembly reveals the karyophilic properties of MA, permitting HIV-1 infection of macrophages.

EXAMPLE 5

HIV-1 MA is also phosphorylated on serine residues

In vivo labelling of virions produced from cultures transfected with wild type R7 and $Y_{132}F$ mutant proviruses with inorganic $^{32}$phosphorous, followed by immunoprecipitation of MA, surprisingly demonstrated incorporation of radiolabel into this protein at almost similar levels in both wild-type (R7) and mutant ($Y_{132}F$) forms.

Two dimensional phospho-amino acid analysis recovered large amounts of phosphoserine from $R_7$ and $Y_{132}F$-derived MA, and phosphotyrosine from R7 MA only. Preliminary data from two dimensional tryptic phosphopeptide maps indicate up to three phosphorylated tryptic peptides in R7 MA. HPLC fractionation of large-scale tryptic digests of $^{32}$P labelled MA, coupled to amino acid sequencing, are employed to map the locations of the phosphorylation sites. Partial tryptic digests of the full-length protein indicate that, in addition to the tyrosine residue at position 132, one serine located in the central region of MA is the main phosphorylation site in this protein.

EXAMPLE 6

In vitro phosphorylation assays reveal high levels of MA-specific kinase in membrane-enriched cell extracts, in conditioned medium, and in HIV-1 particles MA tyrosine phosphorylation is independent from the expression of the viral RT, In, vif, vpr, tat, rev, vpu, env and nef genes, and from the incorporation of the viral RNA in particles. A cellular kinase is responsible for this event. Indeed, in vitro kinase assays employing recombinant matrix protein (i.e., wild-type and $Y^{132}F$) using $^{32}$P-γ-ATP and a crude lymphoblastoma cytoplasmic extract (i.e., a high speed pellet of fresh RPMI-1640 containing 10% FCS (PM), or a high speed pellet of conditioned RPMI-1640 medium from CEM cells (PCM)), followed by phosphoamino acid analyses, confirm that a cellular activity transfers phosphate moieties from $^{32}$P-γ-ATP to tyrosine and serine residues of MA. Furthermore, the preparation of membrane-enriched and cytosolic fractions indicates that the majority of MA-specific kinase activity is associated with cellular membranes. However, the greatest levels of serine and tyrosine kinase activities in these assays is detected in a high speed pellet from medium in which the lymphoblastoma cells are cultured, and to a lesser extent when fresh complete medium is used, indicating that the kinase activity is found in serum.

Significant levels of kinase activity is also found in purified preparations of virions from a chronically infected lymphoblastoma cell line. MA-specific kinase activity is associated with HIV-1 virions. Thus, in vitro phosphorylation of recombinant MA is observed, using $^{32}$P-γ-ATP and fractions from a Sephacryl S-1000 gel filtration purification of virions from chronically infected Molt-IIIB cells. The phospho-amino acid content of MA labelled by these preparations and the pattern of tryptic phosphopeptides has been examined, and found to be similar to those observed in virus-associated MA.

EXAMPLE 7

Cloning and expression of HIV-1 Matrix protein

A cDNA encoding the open reading frame of the HIV-1 matrix protein (i.e., nucleotides 789–1184 of the proviral construct HXB2-R7 (see Trono, Cell 59:113 (1989)), obtained by PCR amplification of plasmid DNA, was subcloned into the NdeI and BamHI sites of the bacterial expression vector pET-15b (Novagen). This bacterial expression vector allows the production of recombinant proteins carrying an N-terminal histidine affinity tag. Following transformation into E. coli BL21/DE3, expression of the recombinant protein was induced using 1 mM isopropyl β-D-thiogalactopyranoside (IPTG). The matrix protein was then purified from the soluble fraction by affinity chromatography on a nickel-Sepharose column according to the manufacturer's instructions. The integrity of the complete matrix cDNA in the expression vector, pET-15b-MA was confirmed prior to the production of recombinant protein by dideoxy sequencing using the T7 promoter and T7 terminator primers (Novagen) which hybridize 5' and 3' to the cloned sequence, respectively.

EXAMPLE 8

In vitro kinase assay

Cellular extract (25–50 μg of protein from CEM human T-lymphoid cell line) in up to 100 μl of assay buffer (50 mM Tris-Cl (pH 7.5), 10 mM $MgCl_2$, 50 mM NaCl, 100 μM $Na_3VO_4$, 0.1% (v/v) Nonidet P-40 and 5 mM $MnCl_2$) was mixed with 20–40 μCi of $^{32}$P-γ-ATP (6000 Ci/mmol), and an inhibitory compound, such as heparin (~100 μg/ml) or 5,6-dichlorobenzimidazole riboside (~100 μM), and kept on ice. The kinase reaction was started by the addition of substrate, i.e., recombinant matrix protein (~3 μg) bearing a 20 amino acid N-terminal histidine affinity tag (prepared as described in Example 7) and incubated at 30° C. for 60 minutes.

The reaction was terminated by dilution to 1 ml with 1x binding buffer (20 mM Tris-Cl (pH 7.9), 500 mM NaCl and 5 mM imidazole). Matrix protein was then recovered by the addition of 40 μl of a suspension of nickel-charged histidine affinity resin (Novagen), prepared according to the manufacturer's instructions, and incubation on a rotating platform for 20 min at 4° C. Following brief centrifugation (i.e., ~2 min at 1000 xg), the supernatant was removed and the pellet containing bound matrix protein was washed in 1 ml of 1x binding buffer for 20 min at 4° C. on a rotating platform, and again in 1 ml of 1x wash buffer (20 mM Tris-Cl (pH 7.9), 500 mM NaCl and 50 mM imidazole). The matrix protein was dissociated from the affinity resin with 30 μl of 1x elution buffer (20 mM Tris-Cl (pH 7.9), 500 mM NaCl and 1 mM imidazole). After brief centrifugation, the supernatant was removed and mixed with 6 μl of 6x SDS loading buffer (300 mMTris-Cl (pH 6.8), 600 mM DTT and 12% SDS) and 60% (v/v) glycerol, and resolved by electrophoresis through a 12.5% SDS polyacrylamide gel. Gels were stained with 0.05% (w/v) Coomassie Brilliant Blue G-250 in $dH_2O$ containing 12.5% (v/v) propan-2-ol and 10% (v/v) glacial acetic acid and de-stained in the same solution lacking dye, then dried under vacuum and subjected to autoradiography. For further analysis of phosphorylated protein, gels were electro-blotted to a polyvinylidene difluoride (PVDF) membrane at 150 mA for 14 hours in transfer buffer (25 mM Tris pH 7.5, 192 mM glycine and 20% methanol), and the protein located by autoradiography.

While the invention has been described in detail with reference to certain preferred embodiments thereof, it will be understood that modifications and variations are within the spirit and scope of that which is described and claimed.

| SEQUENCE LISTING | |
| --- | --- |
| SEQ ID NO:1 | Gly—Lys—Lys—Lys—Try—Lys |
| SEQ ID NO:2 | PKKKRKV |

That which is claimed is:

1. A method for identifying compounds that inhibit tyrosine phosphorylation of human immunodeficiency virus type 1 Matrix protein (MA), said method comprising:

exposing MA to tyrosine phosphorylation conditions independently in the presence, and in the absence, of test compound, detecting the level of tyrosine phosphorylation of MA upon exposure of MA to said test compound, and identifying those test compounds which cause a reduced level of tyrosine phosphorylation of MA as compounds that inhibit tyrosine phosphorylation of MA.

2. A method according to claim 1 wherein said MA is recombinantly produced.

3. A method according to claim 1 wherein said phosphorylation conditions comprise contacting said MA with a cell extract derived from human T cell lines, fibroblasts, epithelial cells or serum.

4. A method according to claim 1 wherein said test compound is selected from antibiotics, anti-fungal agents, anti-neoplastic agents, enzymatically active agents, immunostimulating agents or immunosuppressive agents.

5. A method according to claim 1 wherein MA is contacted with test compound at a concentration in the range of about 0.01 nM up to 10 μM.

6. A method according to claim 1 wherein the phosphorylation of MA is detected employing ELISA, Western blot or uptake of labelled phosphate.

7. A method for identifying compounds that inhibit tyrosine phosphorylation of human immunodeficiency virus type 1 Matrix protein (MA), said method comprising:

exposing MA to tyrosine phosphorylation conditions in the presence of varying amounts of test compound, detecting the level of tyrosine phosphorylation of MA upon exposure of MA to varying amounts of test compound, and identifying those test compounds which cause a reduced level of tyrosine phosphorylation of MA as compounds that inhibit tyrosine phosphorylation of MA.

8. A method according to claim 7 wherein said MA is recombinantly produced.

9. A method according to claim 7 wherein said phosphorylation conditions comprise contacting said MA with a cell extract derived from human T cell lines, fibroblasts, epithelial cells or serum.

10. A method according to claim 7 wherein said test compound is selected from antibiotics, anti-fungal agents, anti-neoplastic agents, enzymatically active agents, immunostimulating agents or immunosuppressive agents.

11. A method according to claim 7 wherein MA is contacted with test compound at a concentration in the range of about 0.01 nM up to 10 μM.

12. A method according to claim 7 wherein the phosphorylation of MA is detected employing ELISA, Western blot or uptake of labelled phosphate.

\* \* \* \* \*